(12) United States Patent
Krishnamoorthy et al.

(10) Patent No.: US 7,785,624 B2
(45) Date of Patent: Aug. 31, 2010

(54) PHARMACEUTICAL LATRUNCULIN FORMULATIONS

(75) Inventors: Ramesh Krishnamoorthy, Cary, NC (US); Leo A. Trevino, Hurdle Mills, NC (US); Richard M. Evans, Cary, NC (US); Carole Evans, legal representative, Cary, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 11/680,893

(22) Filed: Mar. 1, 2007

(65) Prior Publication Data

US 2007/0225343 A1 Sep. 27, 2007

Related U.S. Application Data

(60) Provisional application No. 60/779,273, filed on Mar. 2, 2006.

(51) Int. Cl.
*A61K 31/427* (2006.01)
*A61K 9/20* (2006.01)

(52) U.S. Cl. .................... 424/464; 514/369

(58) Field of Classification Search .............. None
See application file for complete search history.

(56) References Cited

U.S. PATENT DOCUMENTS

| | | | |
|---|---|---|---|
| 5,422,116 A | 6/1995 | Yen et al. | |
| 5,798,380 A | 8/1998 | Kaufman et al. | |
| 6,110,912 A | 8/2000 | Kaufman et al. | |
| 6,586,425 B2 * | 7/2003 | Kaufman et al. | 514/218 |
| 2002/0045585 A1 | 4/2002 | Kaufman et al. | |
| 2003/0165545 A1 * | 9/2003 | Huth et al. | 424/400 |
| 2003/0203849 A1 * | 10/2003 | Araki et al. | 514/17 |

FOREIGN PATENT DOCUMENTS

EP 0480690 A1 4/1992
WO WO 2006-104897 A2 10/2006

OTHER PUBLICATIONS

Jerdeva et al., J. Cell Science, 2005, 118, 4797-4812.*
Okka et al., Arch Ophthalmol, 2004, 122, 1482-1488.*
Molecular Probes, 2005, 1-2.*
Challa et al., AAPS PharmSciTech, 2005, 6(2), E329-E357.*
Sabanay et al.: "Latrunculin B Effects on Trabecular Meshwork and Corneal Endothelial Morphology in Monkeys", Experimental Eye Research, vol. 82 (2006), pp. 236-246.
D. Blasberger, et al., *Liebigs Ann. Chem.*, (1989) 1171-1188.
A. Fürstner et al., *Angew. Chem. Int. Ed.*, (2003) 42, 5358-5360.
A. Fürstner, et al., *PNAS*, (2005) 102: 8103-8108.
Okka, et.al., *Trans. Am. Ophthalmol. Soc.*, (2004) 102: 251-259.
A.B. Smith III et al., *J. Am. Chem. Soc.*, (1992) 114, 2995-3007.
J.D. White and M. Kawasaki, *J. Org. Chem.*, (1992) 57, 5292-5300.
Okka et al., "Effect of Low-Dose Latrunculin B on Anterior Segment Physiologic Features in the Monkey Eye", (Reprinted) Arch Ophthalmol., vol. 122, Oct. 2004, pp. 1482-1488.

* cited by examiner

*Primary Examiner*—Sharmila Gollamudi Landau
*Assistant Examiner*—Kyle Purdy
(74) *Attorney, Agent, or Firm*—Howrey LLP; Viola T. Kung (57) ABSTRACT

The present invention relates to an aqueous pharmaceutical formulation comprising at least one latrunculin and the formulation does not contain a substantial amount of dimethyl sulfoxide. In one embodiment, the present invention is directed to an aqueous pharmaceutical formulation comprising at least one latrunculin in an amount of 0.001-2% w/v, a non-ionic surfactant in an amount of 0.01-2% w/v, and a tonicity agent to maintain a tonicity between 200-400 mOsm/kG, at a pH between 4 to 8, wherein the latrunculin, the surfactant, and the tonicity agent are compatible in the formulation, and the formulation does not contain a substantial amount of dimethyl sulfoxide. The formulation is stable for at least six month at refrigerated temperature. The present invention further provides a method of reducing intraocular pressure, a method of treating glaucoma, a method of inhibiting wound healing after trabeculectomy, and a method of inhibiting angiogenesis.

22 Claims, 3 Drawing Sheets

PHARMACEUTICAL LATRUNCULIN FORMULATIONS

The present application claims the benefit of U.S. Provisional Application 60/779,273, filed Mar. 2, 2006, which is incorporated herein by reference in its entirety.

TECHNICAL FIELD

This invention relates to pharmaceutical formulations, particularly ophthalmic formulation, of macrocylic cytoskeletal active compounds, such as latrunculin compounds and their related analogs. This invention also relates to methods of using such pharmaceutical formulations in the prevention or treatment of diseases or disorders that are affected by modification of the integrity of the actin cytoskeleton, for example, treatment of disorders in which intraocular pressure is elevated, such as primary open-angle glaucoma and ocular neuroprotection in humans and other mammals.

BACKGROUND OF THE INVENTION

Glaucoma is an ophthalmic disease that leads to irreversible visual impairment. It is the fourth most common cause of blindness and the second most common cause of visual loss in the United States, and the most common cause of irreversible visual loss among African-Americans. Generally speaking, the disease is characterized by a progressive neuropathy caused at least in part by deleterious effects resulting from increased intraocular pressure on the optic nerve. Open-angle glaucoma constitutes approximately 90% of all primary glaucoma and is characterized by abnormally high resistance to fluid (aqueous humor) drainage from the eye. Normal resistance is required to maintain an intraocular pressure sufficient to maintain the shape of the eye for optical integrity. This resistance is provided by the trabecular meshwork, a complex tissue consisting of specialized endothelial cells, connective tissue beams and extracellular matrix. The resistance of the trabecular meshwork normally is such that intraocular pressure is ~16 mm Hg, a pressure at which aqueous humor leaves the eye at the same rate at which it is produced (2.5 µL/minute). Extremely high pressures (e.g., 70 mm Hg.) may cause blindness within only a few days. See P. L. Kaufman and T. W. Mittag, "Medical Therapy Of Glaucoma," Ch. 9, Sec. II (pp. 9.7-9.30), in P. L. Kaufman and T. W. Mittag (eds.): Glaucoma (Vol. 7 of S. M. Podos and M. Yanoff (eds): Textbook of Ophthalmology Series). London, Mosby-Year Book Europe Ltd. (1994); A. C. Guyton, Textbook of Medical Physiology (W. B. Saunders Co., Sixth Ed.), pp. 386-89 (1981).

Currently, the treatment of glaucoma and controlling of elevated intraocular pressure is approached using a variety of therapeutic agents across a wide spectrum of chemical classes.

The drug classes most frequently employed to reduce intraocular pressure rely on suppression of aqueous humor formation (e.g., beta-blockers, α2 adrenergic agonists, carbonic anhydrase inhibitors) or enhancement of uveoscleral outflow (prostaglandin analogues). There are no current anti-glaucoma drugs in common use that act directly on the trabecular meshwork. Pilocarpine reduces flow resistance through the trabecular meshwork secondarily, based on meshwork deformation consequent to drug-induced ciliary muscle contraction, but its use is limited by the need for 3-4 times daily administration and local side effects, especially miosis. Epinephrine apparently acts directly on the meshwork cells to increase facility via a β2 adrenergic receptor-mediated pathway, but is seldom used clinically because of receptor-mediated local and systemic side effects, a high frequency of local allergy, and only modest efficacy and inter-patient variability in responsiveness.

Trabeculectomy is the most common form of glaucoma filtration surgery and remains as the first-line therapy for surgical reduction of pharmacologically uncontrolled intraocular pressure in primary open angle glaucoma. This procedure establishes a limbal fistula through which aqueous humor drains into the subconjunctival space establishing a filtering bleb to lower intraocular pressure. The success of the procedure is highly dependent on pharmacological modulation of wound healing.

A major advance in the surgical management of glaucoma has been the use of antimetabolites to prevent scarring after glaucoma filtration surgery. Postoperative scarring of the filtering bleb is the most crucial factor in determining the short and long-term outcome of modern glaucoma filtration surgery. Antimetabolites mitomycin C (MMC) and 5-fluorouracil (5-FU) are the most widely used agents to suppress scarring and the failure of the filtering bleb. In a large retrospective study, conventionally performed trabeculectomy has shown a failure rate of up to 30% within 3 months after surgery. To lower the incidence of this detrimental complication, various methods have been investigated in order to avoid the naturally occurring scarring of the filtering bleb, mostly dealing with the intraoperative or postoperative application of antimetabolic drugs—that is, 5-fluorouracil (5-FU) or mitomycin C (MMC), the two most widely used cytotoxic agents.

Despite their positive long-term effect on prolonged filtration, the application of cytotoxic drugs to a surgically opened eye increases the incidence of severe complications such as concomitant increases in vision threatening complications. MMC and 5-FU exhibit a high incidence of severe post-application complications; their side effects mainly affect the corneal epithelium and their clinical uses are limited by severe pain and discomfort to the patient. No sufficient method has been established to achieve satisfying postoperative long term surgical results with only minimal or no side effects for the patient.

U.S. Pat. Nos. 6,586,425; 6,110,912; and 5,798,380 disclose a method for the treatment of glaucoma using compounds that affect the actin filament integrity of the eye to enhance aqueous humor outflow. These patents also specifically disclose kinase inhibitors and latrunculin-A, latrunculin-B, swinholide-A, and jasplakinolide, which cause a perturbation of the actin cytoskeleton in the trabecular meshwork or the modulation of its interactions with the underlying membrane. Perturbation of the cytoskeleton and the associated adhesions reduces the resistance of the trabecular meshwork to fluid flow and thereby reduces intraocular pressure.

Latrunculins are soluble in dimethyl sulfoxide (DMSO), but they have a very low aqueous solubility, due to the largely lipophilic nature of the latrunculins that are large macrocylic compounds. DMSO is not permissible in an ophthalmic formulation for human use. Latrunculin-B is typically dissolved in DMSO as a stock solution, and stored at −20° C. for long-term stability (Okka, et. al., *Trans. Am. Ophthalmol. Soc.* 102: 251-259 (2004)). Known liquid latrunculin formulations are not acceptable pharmaceutical formulations because of one or more of the following problems: unwanted side affects such as toxicity due to vehicle or adjuvant, low solubility of the latrunculin without the use of DMSO, and poor stability due to latrunculin degradation over time.

There exists a need for a pharmaceutical formulation that can be used to treat glaucoma, to modulate wound healing after trabeculectomy, and to treat other diseases or disorders that are affected by the integrity of the actin cytoskeleton.

SUMMARY OF THE INVENTION

The present invention is directed to an aqueous pharmaceutical formulation comprising at least one latrunculin and the formulation does not contain a substantial amount of dimethyl sulfoxide. The present invention provides an aqueous pharmaceutical formulation comprising at least one latrunculin and one or more agents that enhance the solubility of latrunculins in an aqueous medium. The formulation does not contain a substantial amount of any unacceptable agents for pharmaceutical, particularly, ophthalmic use. The formulation provides latrunculins with a sufficient activity for therapeutical use and is stable for at least six months at refrigerated temperature.

The present invention is directed to an aqueous pharmaceutical formulation comprising at least one latrunculin in an amount of 0.001-2% w/v, a non-ionic surfactant in an amount of 0.01-2% w/v, and a tonicity agent to maintain a tonicity between 200-400 mOsm/kG, at a pH between 4 to 8, wherein the latrunculin, the surfactant, and the tonicity agent are compatible in the formulation, and the formulation does not contain a substantial amount of dimethyl sulfoxide.

In one embodiment, the aqueous pharmaceutical formulation comprises at least one latrunculin in an amount of 0.001-2% w/v, 1-100 mM buffer suitable to maintain the pH between 4-6, 0.01-2% w/v non-ionic surfactant, and a tonicity agent to maintain a tonicity between 200-400 mOsm/kG. A preferred buffer is citrate buffer. Preferred tonicity agents are mannitol and dextrose.

In another embodiment, the aqueous pharmaceutical formulation comprises at least one latrunculin in an amount of 0.001-2% w/v, 5-10% ethanol and a tonicity agent to maintain a tonicity between 200-400 mOsm/kG. The formulation optionally comprises 1-100 mM buffer to maintain the pH between 4-8.

In yet another embodiment, the aqueous pharmaceutical formulation comprises at least one latrunculin in an amount of 0.001-2% w/v, 1-10% polypropylene glycol, 0.02-0.25% polaxamer, 0.1-1% polysorbate, and a tonicity agent to maintain a tonicity between 200-400 mOsm/kG, wherein the pH of the formulation is 4-8.

In yet another embodiment, the aqueous pharmaceutical formulation comprises 0.001-2% latrunculin, a cyclodextrin, 0.01-0.5% preservative, and a tonicity agent to maintain a tonicity between 200-400 mOsm/kG, wherein the pH of the formulation is 4-8.

The present invention provides a method of reducing intraocular pressure, a method of treating glaucoma, a method of inhibiting wound healing after trabeculectomy, and a method of inhibiting angiogenesis. The method comprises the step of administering to a subject in need of treatment the aqueous pharmaceutical formulation of the present invention, in an amount effective to alter the actin cytoskeleton, for example, by inhibiting actin polymerization.

DETAILED DESCRIPTION OF THE INVENTION

Unless otherwise specified, the % amount in this application refers to % (w/v).

The inventors have discovered an aqueous latrunculin formulation that does not require the use of DMSO. The inventors have discovered a non-DMSO aqueous latrunculin formulation that is stable for a significant period of time at room temperature and refrigerated temperature. The inventors have discovered an aqueous latrunculin formulation that is useful for the treatment of certain conditions by inhibiting the polymerization of actin filaments, such as glaucoma. The inventors have discovered an aqueous latrunculin formulation that is well tolerated for ocular use.

This invention is directed to an aqueous pharmaceutical formulation comprising a macrocylic compound, specifically latrunculins and latrunculin analogs. This invention provides a formulation containing one or more agents that enhance the solubility of latrunculin compounds in an aqueous medium. The formulation does not contain a substantial amount of unacceptable agents for pharmaceutical, particularly, ophthalmic uses. The invention provides a stable aqueous formulation of latrunculins; the formulation is suitable for therapeutic use and remains stable under normal use storage conditions for an extended period of time.

The aqueous pharmaceutical formulations of the present invention exclude the use of inappropriate solubilizing adjuvants such as methanol and dimethylsulfoxide, which can cause toxicological outcomes and tissue damage when used in humans or mammals for a long term. These pharmaceutical formulations contain latrunculins in an aqueous solution at a sufficient concentration, and show a pharmacological effect on lowering intraocular pressure in mammals. For topical administration, one to two drops of these formulations are delivered to the surface of the eye one to four times per day according to the routine discretion of a skilled clinician. These aqueous pharmaceutical formulations are non-irritating and tolerable to the eyes, and are suitable for multiple instillation.

Latrunculins are cytoskeletal active macrolides. Latrunculins are specific and potent actin-disrupting agents that sequester monomeric G-actin, leading to the disassembly of actin filaments. Natural latrunculins are isolated from marine sponges such as *Latrunculia magnifica, Negombata magnifica*, and *Spongia mycofijiensis*, and from nudibranches, for example *Chromodoris lochi*. Latrunculin analogs can be prepared by synthetic methods (A. B. Smith III et al., *J. Am. Chem. Soc.* 1992, 114, 2995-3007; J. D. White and M.

Kawasaki, *J. Org. Chem.* 1992, 57, 5292-5300; A. Fürstner et al., *Angew. Chem. Int. Ed.* 2003, 42, 5358-5380).

Latrunculins, as used in this application, refer to natural latrunculins and latrunculin analogs. Prefer latrunculins of this invention are latrunculin B, latrunculins A, des-methyl latrunculin B, or a pharmaceutically acceptable salt, tautomer, solvate, or hydrate thereof.

Latrunculin B

Latrunculin A
Lat A des-methyl latrunculin B

Latrunculin analogs, as used in this application, refer to synthetic compounds whose structures are similar to those of natural latrunculins, as disclosed in D. Blasberger, et al., *Liebigs Ann. Chem.* 1171-1188 (1989); Fürstner, et al., *PNAS*, 102: 8103-8108 (2005); and U.S. Patent Publication US2006-0217427; the contents of which are incorporated herein by references.

The present invention is directed to an aqueous pharmaceutical formulation comprising at least one latrunculin and the formulation does not contain a substantial amount of dimethyl sulfoxide. As used herein, "a substantial amount" refers to more than 0.1%, preferably 0.01%, and more preferably 0.001%. The aqueous pharmaceutical formulation of the present invention does not contain more than 0.1%, preferably 0.01%, and more preferably 0.001% v/v of DMSO. In a preferred embodiment, the aqueous pharmaceutical formulation of the present invention does not contain any dimethyl sulfoxide.

The present invention is directed to an aqueous pharmaceutical formulation comprising at least one latrunculin in an amount of 0.001-2% w/v, and a tonicity agent to maintain a tonicity between 200-400 mOsm/kG, wherein the pH of the formulation is 4-9, and the formulation does not contain a substantial amount of dimethyl sulfoxide. When the pharmaceutical formulation is used opthalmically, the pH of the formulation is preferably 4-8, and the tonicity is preferably 220-380 mOsm/kG.

The present invention is directed to an aqueous pharmaceutical formulation comprising at least one latrunculin in an amount of 0.001-2% w/v, 1-100 mM of a buffer suitable to maintain the pH between 4-8, preferably to maintain pH between 4-6, 0.01-2% w/v of a non-ionic surfactant, and a tonicity agent to maintain a tonicity between 200-400 mOsm/kG. This pharmaceutical formulation does not contain a substantial amount of DMSO and preferably contains no more than 5% (v/v) ethanol, and more preferably no more than 2%, 1%, of ethanol.

It is important that the components of the present formulation are compatible with each other. Compatible, as used herein, refers to physical compatibility and chemical compatibility. Physical compatibility means that the components do not form precipitates or coacervates, and do not cause phase separation, settling, or discoloration. Chemical compatibility means that the components do not cause degradation of latrunculins or inactivate the biological activity of latrunculins.

Surfactants (surface active agents) suitable for the present invention can be non-ionic or ionic. However, ionic surfactants are less preferred. Long term use of cationic agents, especially cationic surfactants, is well known to cause corneal epithelial damage. Anionic surfactants are often non-compatible with other components of the present formulation.

Preferred surfactants for the present invention are non-ionic. Suitable non-ionic surfactants include, but are not limited to polysorbate 80, polysorbate 60, polysorbate 20, tyloxapol, polyoxyl stearates, glyceryl monostearate, polyoxyl castor oil, polyethylene glycol caprylic triglyceride, and poloxamers. Preferred non-ionic surfactants are polysorbates and poloxamers. These surfactants are nonionic alkaline oxide condensates of an organic compound that contains hydroxyl groups. Non-ionic surfactants enhance the solubility of latrunculins. Non-ionic surfactants often protect the latrunculin molecules from chemical degradation by holding the latrunculin molecules in a micellar environment, which improves the physical and chemical stability. The concentration of the surfactant(s) in the formulation is about 0.01-2%, preferably 0.05-1.5%, and more preferably 0.1-1% (w/v). The proper concentration of the surfactant is determined by the solubility of the latrunculin in the presence of the surfactant, by neutralization of the bactericidal effects on the accompanying preservatives, and/or by the concentrations that may cause irritation to a human. The pharmaceutical formulations made in the presence of a non-ionic surfactant can be adjusted to a target pH of 4-8 without compromising the solubility of latrunculins.

Not all non-ionic surfactants are suitable for the latrunculin formulation, due to their non-compatibility with latrunculins or other components in the formulation, or due to their unsuitability for human use. For example, non-ionic surfactants such as sorbitan monostearate, sorbitan trioleate, sorbitan monooleate, polyethylene glycol glyceryl cocoate, and oleth class of surfactants are not compatible with the latrunculin formulation because these surfactants do not form a clear solution and form coacervates and/or precipitates when admixed with other components of the formulation. Also, non-ionic surfactant TRITON® (polyoxyethylene octyl phenyl ether) is not suitable for human use.

The concentration of latrunculin(s) in the aqueous formulation is in general 0.001-2%, preferably 0.005-0.2%, more preferably 0.005-0.1%, and more preferably 0.005-0.02% (w/v).

Buffers suitable to maintain the pH between 4-8 include phosphate, citrate buffer, acetate buffer, maleate buffer, tartarate buffer, or combination thereof. Phosphate buffer or citrate buffer is preferred. For long-term stability, the formulation is preferred to have a pH of 4-6. Buffers suitable to maintain the pH between 4-6 include citrate buffer, acetate buffer, citrate/phosphate buffer, maleate buffer, tartarate buffer, or combination thereof. Suitable concentration of the buffer is 1-100 mM, preferably 5-50 mM, more preferably 5-25 mM, and most preferably 10-20 mM.

The tonicity agent is present in an amount to achieve a tonicity between 200-400, preferably 220-380, and more preferably 250-340 mOsm/kG. The tonicity agent can be non-ionic or ionic. A non-ionic tonicity agent is preferred because it is often more compatible with surfactants than an ionic tonicity agent. Non-ionic tonicity agents include diols, such as glycerol, mannitol, erythritol; and sugars such as dextrose. Other non-ionic tonicity agents such as glycerol, polyethylene glycol, propylene glycol, which also function as cosolvents, can also be used. The non-ionic tonicity agent is in general in an amount of 2-20%, preferably 3-10%, more preferably 3.5-5% (w/v). Preferred non-ionic agents are mannitol and dextrose, in an amount of 2-6%.

The tonicity agent can also be ionic agents such as sodium chloride, potassium chloride, or balanced salt solution. The ionic tonicity agents can be present in an amount of 0.5-0.9%, preferably 0.6-0.9% (w/v).

The surfactant, the tonicity agent, the cosolvent, and any other ingredient introduced in the formulation must have a good solubility in water, have compatibility with other components, and have mild effects on the final viscosity of the formulation. The formulation needs to have a proper final viscosity such that the formulation can be delivered as a topical drop using a typical ophthalmic dropper bottle and is filter-sterilizable. The formulation is preferably a clear solution without any precipitate.

The pharmaceutical formulation of the present invention optionally comprises a chelating agent. A chelating agent is a substance which can form several coordinate bonds to a metal ion. Chelating agents offers a wide range of sequestrants to control metal ions in aqueous systems. By forming stable water-soluble complexes with multivalent metal ions, chelating agents prevent undesired interaction by blocking normal reactivity of metal ions. Ethylenedinitrilotetraacetic acid (EDTA), diethylenetriaminepentaacetic acid (DTPA), and N,N-bis(carboxymethyl)glycine (NTA) are examples of chelating agents for the present inventions. EDTA (ethylenediamine tetraacetate) is a preferred chelating agent.

Health regulations in various countries require that multi-dose ophthalmic preparations include a preservative. Many well known preservatives that have been used in some other ophthalmic preparations cannot be used in the present invention, because those preservatives are not considered safe for repeatedly ocular use, or they interact with the surfactant employed herein to form a complex, which reduces the bactericidal activity of the preservative. In one embodiment, benzalkonium chloride is employed as a safe preservative; preferably, benzalkonium chloride is employed with EDTA. Other suitable preservatives included benzyl alcohol, methyl parabens, propyl parabens, thimerosal, chlorobutanol, and benzethonium chlorides. Typically, such preservatives are used at a level of from 0.001-1%, preferably, 0.01-0.25%, and most preferably 0.05-0.2% (w/v).

In one embodiment, the pharmaceutical formulation comprises 0.5-0.9% ionic tonicity modifier such as sodium chloride; the formulation contains additional buffering agents (such as sodium phosphates and/or sodium citrate and citric acid) at 1-100 mM, an non-ionic surfactant within a range of 0.01-2%, a chelating agent in a range of 0.005-0.5% w/v, and pH adjusters. Such an aqueous composition has a tonicity of 250-350 mOsm/kG and is formulated at pH 4-6.

In one embodiment, the pharmaceutical formulation comprises 4-5% non-ionic tonicity agent such as mannitol; the formulation contains buffering agents (such as sodium phosphates and/or sodium citrate and citric acid) within a range of 5-50 mM, a surfactant within a range of 0.01-2%, a chelating agent in a range of 0.005-0.5% w/v, and pH adjusters. Such an aqueous composition has a tonicity of 250-350 mOsm/kG and is formulated at pH 4-6. The formulation optionally contains a preservative in a range of 0.001-0.1% w/v.

In one embodiment, the pharmaceutical formulation comprises 0.001-2% w/v of a latrunculin, 0.1-2% polysorbate 80, and a tonicity agent to maintain a tonicity between 200-400 mOsm/kG. The formulation optionally comprises 1-100 mM buffer to maintain the pH between 4-6. Suitable buffer include phosphate, citrate buffer, acetate buffer, maleate buffer, tartarate buffer, or combination thereof. Phosphate or citrate buffer is preferred.

The present invention is further directed to an aqueous pharmaceutical formulation comprising at least one latrunculin in an amount of 0.001-2% w/v, 5-25% ethanol (v/v) and a tonicity agent to maintain a tonicity between 200-400 mOsm/kG. For ophthalmic application, the ethanol concentration is preferred to be 5-10%. The formulation optionally comprises 1-100 mM buffer to maintain the pH between 4-8. Suitable buffer include phosphate, citrate buffer, acetate buffer, maleate buffer, tartarate buffer, or combination thereof. Phosphate buffer or citrate buffer is preferred. The formulation does not contain a substantial amount of DMSO. In one embodiment, the formulation contains 0.005-0.02% latrunculin, 5-10% ethanol, and 0.5-0.9% sodium chloride.

The present invention is further directed to an aqueous pharmaceutical formulation comprising at least one latrunculin in an amount of 0.001-2% w/v, 1-10% (v/v) propylene glycol, 0.02-0.25% (w/v) polaxamer, and a tonicity agent to maintain a tonicity between 200-400 mOsm/kG. The formulation optionally comprises 1-100 mM buffer to maintain the pH between 4-8, and/or 0.1-1% surfactant such as polysorbate 80. Suitable buffer include phosphate, citrate buffer, acetate buffer, maleate buffer, tartarate buffer, or combination thereof. Phosphate buffer or citrate buffer is preferred. The formulation does not contain any DMSO.

The present invention is further directed to an aqueous pharmaceutical formulation comprising at least one latrunculin in an amount of 0.001-2% w/v, a cyclodextrin in an amount of 0.005-5%, preferably 0.01-2% w/v, preservative such as benzalkonium chloride in an amount of 0.01-0.5% w/v, and a tonicity agent to maintain a tonicity between 200-400 mOsm/kG. Cyclodextrins that form complexes with latrunculins and increase the aqueous solubility of latrunculin are suitable for the present invention. For example, 0.01-2% hydroxypropyl-beta cyclodextrin or 0.01-1% sulfobutylated ester of hydroxypropyl-beta cyclodextrin are included in the aqueous formulation. The formulation optionally comprises 1-100 mM buffer to maintain the pH between 4-8. Suitable buffer include phosphate, citrate buffer, acetate buffer, maleate buffer, tartarate buffer, or combination thereof. Phosphate or citrate buffer is preferred. The formulation does not contain a substantial amount of DMSO. The formulation optionally comprises a surfactant such TWEEN® (polysorbate)-20, TWEEN® (polysorbate)-40, TWEEN® (polysorbate)-60, Span (sorbitan monooleate)-20, Span (sorbitan monooleate)-40, tyloxapol, polyvinyl pyrrolidone, and polyvinyl alcohol.

The present invention is further directed to an emulsion including microemulsion or dilute emulsion, in which latrunculins are formulated with adjuvants to form a uniform, reproducible, and robust pharmaceutical formulation that is physically and chemically stable. Suitable adjuvants include surfactants, emulsifying agents, and suitable vegetable or synthetic oils that are pharmaceutically acceptable. The emulsion is formulated in an aqueous solution at a pH between 4-8, preferably 4-7, and more preferably between pH 4-6. The formulation optionally comprises 1-100 mM buffer to maintain the pH between 4-8. Suitable buffer include phosphate, citrate buffer, acetate buffer, maleate buffer, tartarate buffer, or combination thereof. Phosphate or citrate buffer is preferred. The formulation does not contain a substantial amount of DMSO. The emulsion optionally contains a suitable preservative and one or more antioxidant agents. Such an emulsion may be prepared using routine emulsification techniques including but not limited to high-shear homogenization, ultrasonication, high pressure homogenization, mechanical agitation followed by high pressure emulsification, or techniques such as microfluidization or fluid-fluid interactions.

In one embodiment, the emulsion formulation comprises 0.001-2% latrunculin, 1-10% castor oil or 10-20% mineral oil, 1-5% carbomers or 1-10% cetyl alcohol, 0.1-1% polysorbate 80, 0.1-1% glyceryl monostearate or 0.1-2% polyoxyl stearate, and a tonicity agent such as glycerin or propylene glycol to maintain a tonicity between 200-400 mOsm/kG; the pH of the formulation is 4-7.

The pharmaceutical formulations of the present invention are stable under refrigerated storage temperature for at least three months, preferably 6 months, and more preferably 12 months. Stable, as used herein, refers to at least 70%, preferably 80%, more preferably 90% of the latrunculin molecules remain intact without degradation.

The pharmaceutical formulations of the present invention are suitable for storage at refrigerated temperature or room temperature, but are not stable when subjected to a freeze-thaw cycles, as exhibited by the non-homogeneity of the latrunculin molecules and changes in the preservative effectiveness of the formulation.

The pharmaceutical formulations of the present invention are made by aseptic technique or are terminally sterilized. The purity levels of all materials used in the preparation exceed 90%. The solutions of the invention are prepared by thoroughly mixing the latrunculin, buffer, tonicity modifier, surfactant, chelating agent; optionally, non-ionic polymers, complexing agents, solubilizing agents, preservatives and antioxidant agent.

The pharmaceutical formulation can be sterilized by filtering the formulation through a sterilizing grade filter, preferably of a 0.22 micron nominal pore size. The pharmaceutical formulation can also be sterilized by terminally sterilization using one or more sterilization techniques including but not limited to a thermal process, or a radiation sterilization process, or using pulsed light to produce a sterile formulation.

In one embodiment, the pharmaceutical formulation of the present invention is administered locally to the eye (e.g., topically, intracamerally, or via an implant) in the form of ophthalmic preparations. The pharmaceutical formulation can be combined with ophthalmologically acceptable viscosity enhancers, or penetration enhancers to form an ophthalmic suspension or solution. The pharmaceutical formulation is ready for use, without further dilution or any other manipulation.

Glaucoma is an ophthalmic disease that leads to irreversible visual impairment. Open-angle glaucoma is characterized by abnormally high resistance to fluid (aqueous humor) drainage from the eye. Adhesions between cells of the trabecular meshwork are major determinants of the resistance to flow. The pharmaceutical formulations of the present invention cause a transient, pharmacological perturbation of cell adhesions, mainly via disruption of the associated cytoskeletal structures or the modulation of their interactions with the membrane. Perturbation of these adhesions reduces the resistance of the trabecular meshwork to fluid flow and thereby reduces intraocular pressure in a therapeutically useful manner.

The pharmaceutical formulations of the present invention are useful for modulation of wound healing after trabeculectomy. The pharmaceutical formulations in general are less toxic to corneal endothelial cells than the antimetabolites such as 5-fluorouracil or mitomycin C. The pharmaceutical formulations inhibit actomyosin-driven contractility, leading to deterioration of the actin microfilament system and perturbation of its membrane anchorage, which weakens the cell-extracellular matrix adhesions. These properties inhibit wound healing and thereby reduce bleb failure following the surgery.

Angiogenesis is characterized by the development of new vasculature from pre-existing vessels and plays a central role in physiological processes such as embryogenesis, wound healing and female reproductive function, as well as pathophysiologic events including cancer, rheumatoid arthritis and diabetic retinopathy. The growth and metastasis of tumors is critically dependent upon angiogenesis. Angiogenesis is a multi-step process involving the endothelial cell (EC) cytoskeleton in migration, proliferation, and barrier stabilization. Applicants believe that interactions between the cytoskeleton and apoptosis are involved in the intracellular pathways by which angiogenic tube formation occurs. The pharmaceutical formulations of the present invention are useful in inhibiting angiogenesis and treating tumors.

Antimitotic drugs markedly interfere with antidiuretic response, strongly implying that cytoskeleton integrity is essential to this function. This role of the cytoskeleton in controlling the epithelial transport is a necessary step in the translocation of the water channel containing particle aggregates and in their delivery to the apical membrane. Regulation of the actin cytoskeleton is important in the modulation of fluid transport. Osmolality-dependent reorganization of the cytoskeleton and expression of specific stress proteins are important components of the regulatory systems involved in the adaptation of medullary cells to osmotic stress. The pharmaceutical formulations of the present invention are useful in directing epithelial function and modulating fluid transport.

The present invention provides a method of reducing intraocular pressure, a method of treating glaucoma, a method of inhibiting wound healing after trabeculectomy, a method of inhibiting angiogenesis, a method of treating cancer, and a method of directing epithelial function and modulating fluid transport. The method comprises the step of administering to a subject in need of treatment the pharmaceutical formulation of the present invention, in an amount effective to alter the actin cytoskeleton, such as by inhibiting actin polymerization.

The pharmaceutical formulation of the present invention are useful as agents for lowering intraocular pressure, and are thus useful in the treatment or prevention of glaucoma or associated ophthalmic conditions.

The pharmaceutical formulation of the present invention is useful in the treatment or prevention of neurodegenerative diseases as a consequence of increased intraocular pressure and damage to the ocular neurons.

The pharmaceutical formulations of the present invention can also be used in the area of cosmetics for reducing wrinkles, in the area of preserving blood platelets, and in the area of vasospasm and smooth muscle spasm by means and route of administration known to those skilled in the art.

The pharmaceutical formulation disclosed herein can be administered to the eyes of a patient topically by any suitable means, but are preferably administered in the form of drops, spray or gel. Alternatively, the pharmaceutical formulation can be applied to the eye via liposomes. Further, the pharmaceutical formulation can be infused into the tear film via a pump-catheter system. In another embodiment, the pharmaceutical formulation is contained within a continuous or selective-release device, for example, membranes such as, but not limited to, those employed in the Ocusert™ System (Alza Corp., Palo Alto, Calif.) or Retisert (Bausch & Lomb, Rochester, N.Y.). As an additional embodiment, the pharmaceutical formulation can be contained within, carried by, or attached to contact lenses that are placed on the eye. Another embodiment of the present invention involves the pharmaceutical formulation contained within a swab or sponge that can be applied to the ocular surface. Another embodiment of the present invention involves the pharmaceutical formulation contained within a liquid spray that can be applied to the ocular surface. Another embodiment of the present invention involves an injection of the pharmaceutical formulation directly into the lacrimal tissues or onto the eye surface.

In one embodiment, the pharmaceutical formulation is administered systemically to a subject. The term systemic as used herein includes subcutaneous injection, intravenous, intravitreal injection, intracameral injection, subconjunctival injections, topical administration, and oral administration.

Intravitreal delivery can include single or multiple intravitreal injections, or via an implantable intravitreal device that releases cytoskeleton targeting compounds in a sustained capacity. Intravitreal delivery can also include delivery during surgical manipulations as either an adjunct to the intraocular irrigation solution or applied directly to the vitreous during the surgical procedure. A similar approach may be taken for a subconjunctival or retrobulbar injection.

The invention is illustrated further by the following examples that are not to be construed as limiting the invention in scope to the specific procedures described in them. Without further elaboration, it is believed that one skilled in the art can, using the preceding description, utilize the present invention to its fullest extent. The following preferred specific embodiments therefore are to be construed as merely illustrative, and not limited of the remainder of the disclosure in any way whatsoever.

EXAMPLES

Example 1

Preparation of Formulation of Latrunculin B, 0.02% in a 5% Ethanol Vehicle Formulation To a vial containing 1 mg of latrunculin B was added 250 microliters of 200 proof ethanol following which the solution was mixed at ambient temperature. To this was added 750 microliters of a phosphate-buffered saline solution whose pH was approximately 7; the solution was admixed at ambient temperature for about 5 minutes. The resulting solution was clear and was 0.1% with respect to latrunculin B. This solution was used as is or diluted to a 0.02% concentration using the phosphate-buffered saline formulation.

Example 2

Preparation of Solution of Latrunculin B in an Aqueous Vehicle Formulation

To a vial containing 1 mg of latrunculin B was added 100 microliters of propylene glycol following which the solution was mixed at ambient temperature. The latrunculin B immediately went into solution. The solution was cooled to approximately 5° C. in an ice-bath. To this was added 450 microliters of a phosphate-buffered saline solution (pH ~7) containing 0.25% w/v polaxamer 407 and mixed for 10 minutes while maintaining the temperature at approximately 5° C. To this was added 450 microliters of a phosphate-buffered saline solution (pH ~7) containing 1% w/v polysorbate 80 and mixed for 10 minutes at ambient temperature conditions. The resulting solution was clear and was 0.1% with respect to latrunculin B. This solution was used as is or diluted to a 0.02% concentration using the phosphate-buffered saline solution (pH ~7).

Example 3

Preparation of Formulation of Latrunculin B in an Aqueous Vehicle Formulation

To a vial containing 1 mg of latrunculin B was added 50 microliters of propylene glycol and 40 microliters of glycerin following which the solution was mixed at ambient temperature. The latrunculin B went into solution. The solution was cooled to approximately 5° C. in an ice-bath. To this was added 910 microliters of a phosphate buffered saline solution (pH ~7) containing 0.2% w/v poloxamer 407 and 1% w/v polysorbate 80. Following the addition, the solution was admixed at 5° C. for about 10 minutes and then allowed to mix at room temperature for an additional 10 minutes. The resulting solution was clear and was 0.1% with respect to latrunculin B. This solution was used as is or diluted to a 0.02% or lower concentration using the phosphate-buffered saline solution (pH ~7) containing 0.2% w/v poloxamer 407 and 1% w/v polysorbate 80.

Example 4

Preparation of Preserved Preparation of Latrunculin B in an Aqueous Vehicle Formulation To a vial containing 1 mg of latrunculin B was added 1 mL of an approximately 10 mM citrate buffer solution containing 4.5% w/v mannitol, 1% w/v polysorbate 80, 0.05% w/v disodium edetate, and 0.01% w/v benzalkonium chloride (pH ~5.5) and mixed at room temperature for about 15 minutes. The solution was clear and colorless. The solution was 0.1% with respect to latrunculin B and had a pH of approximately 5.5. This solution was used as is or diluted to 0.02% w/v or a lower concentration (such as 0.005% w/v) using the citrate-buffered solution (pH ~5.5) containing 4.5% w/v mannitol, 1% w/v polysorbate 80, 0.05% w/v disodium edetate, and 0.01% w/v benzalkonium chloride.

The solutions containing 0.02% (Solution A) and 0.005% (Solution B) latrunculin B were tested for stability. The degradation of latrunculin B was measured by HPLC. The results show that solution A maintains 95%, and solution B maintains 100% of the initial amount of latrunculin B, after storage at 2-8° C. for 6 months.

Example 5

Preparation of Solution of Des-methyl Latrunculin B, 0.02% in a 5% Ethanol Vehicle Formulation To a vial containing 1 mg of des-methyl-latrunculin B was added 250 microliters of 200 proof ethanol following which the solution was mixed at ambient temperature. To this was added 750 microliters of a phosphate-buffered saline solution whose pH was approximately 7; the solution was admixed at ambient temperature for about 5 minutes. The resulting solution was clear and was 0.1% with respect to latrunculin B. This solution was used as is or diluted to a 0.02% concentration using the phosphate-buffered saline formulation.

Example 6

Preparation of Solution of Cis-des-methyl Latrunculin B in an Aqueous Vehicle Formulation To a vial containing 1 mg of cis-des-methyl latrunculin B was added 1 mL of an approximately 10 mM citrate buffer solution containing 4.5% w/v mannitol, 1% w/v polysorbate 80, 0.05% w/v disodium edetate, and 0.01% w/v benzalkonium chloride (pH ~5.5) and mixed at room temperature for about 15 minutes. The solution was clear and colorless. The solution was 0.1% with respect to latrunculin B and had a pH of approximately 5.5. This solution was used as is or diluted to a 0.02% or lower concentration using the citrate-buffered solution (pH ~5.5) containing 4.5% w/v mannitol, 1% w/v polysorbate 80, 0.05% w/v disodium edetate, and 0.01% w/v benzalkonium chloride.

Example 7

Effects of Formulations of Cytoskeletal Targeting Compounds on Intraocular Pressure In Vivo Animal Preparation and Instrumentation:

For all the in vivo experiments and assessment of tolerability of the formulations and studying the effects of the compounds in these formulations on intraocular pressure, the experiments were conducted in Dutch-belted rabbits. Animals used in these assessments were individually housed in a husbandry wherein they were exposed to a normal, non-reversed 12-hour light and dark cycle and have free access to food and water. The measurement of intraocular pressure was performed using a commercially available TonoPen XL tonometer.

Experimental Protocol:

Rabbits are removed from their cage and restrained in a cloth sac for a few minutes prior to IOP measurements to minimize stress-induced increases in IOP. The corneas of the rabbit eyes are anesthetized with 0.25% proparacaine HCl. After waiting for about 2 minutes to allow the anesthetic to take effect, the eyelid is held open with the non-dominant hand and the Tono-Pen is touched to the central cornea multiple times in succession to register readings. Either a pharmaceutical formulation containing latrunculin B or a control vehicle is administered to each animal as one or more topical eye drop(s). Typically, using a pipette, 20 microliters (2 drops×10 microliters each) is administered to the central cornea at approximately 30 second intervals. Blinking is prevented to maximize penetration; an equal volume of the same test compound solution or vehicle is instilled into both eyes. IOP measurements are made prior to instillation (−1 hour, 0 hour) and 1, 2-2.5, 3, 4.5, and 6 hours post-instillation. Animals are returned to the cage after each series of measurements. In addition to IOP measurements, brief ocular examinations are performed prior to dosing and during the course of the administration and at the end of the study. Evaluations are focused to observe the conditions of the eyes, specifically ocular signs such as redness, chemosis, conjunctival discharge, and corneal opacities.

Results

Figure 1:
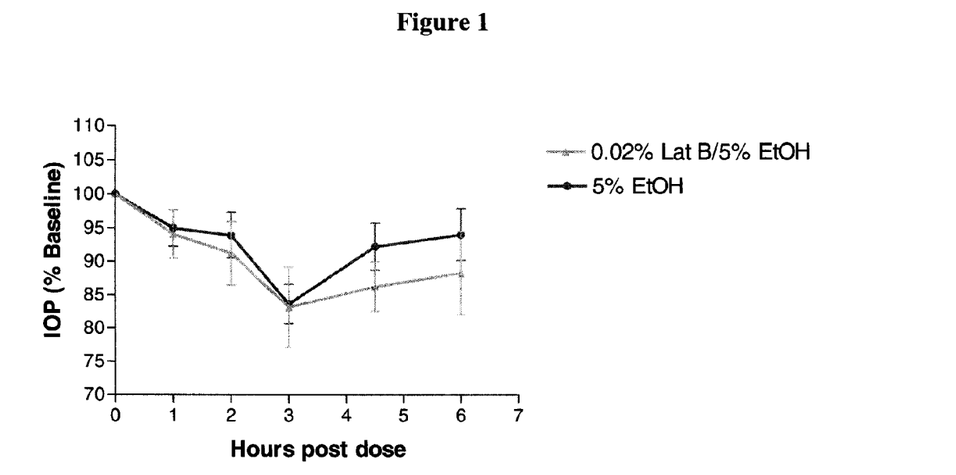
FIG. 1 shows intraocular pressure (IOP, % base line) vs. time post treatment, of Dutch-belted rabbits treated with 0.02% latrunculin B in 5% ethanol formulation, and with vehicle.

FIG. 1 shows the effects of intraocular pressure reduction in Dutch-belted rabbits treated with 0.02% latrunculin B in 5% ethanol formulation and with vehicle.

Figure 2:
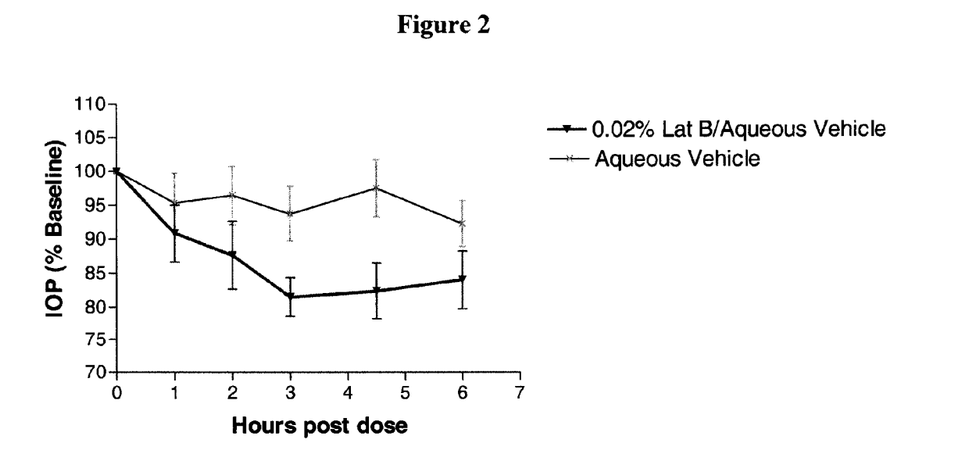
FIG. 2 shows intraocular pressure (IOP, % base line) vs. time post treatment, of Dutch-belted rabbits treated with 0.02% latrunculin B in phosphate-buffered saline solution (pH ~7) containing propylene glycol, poloxamer 407 and polysorbate 80, and with vehicle.

FIG. 2 shows the effects of intraocular pressure reduction in Dutch-belted rabbits treated with 0.02% latrunculin B in phosphate-buffered saline solution (pH ~7) containing propylene glycol, poloxamer 407 and polysorbate 80 and with vehicle (Example 3).

Figure 3:
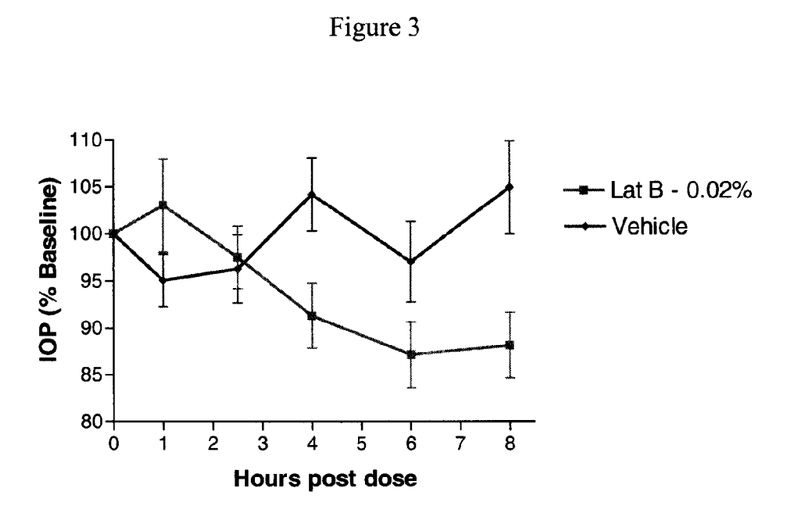
FIG. 3 shows intraocular pressure (IOP, % base line) vs. time post treatment, of Dutch-belted rabbits treated with 0.02% latrunculin B in citrate-buffered solution (pH ~5.5) containing 4.5% w/v mannitol, 1% w/v polysorbate 80, 0.05% w/v disodium edetate, and 0.01% w/v benzalkonium chloride, and with vehicle.

FIG. 3 shows the effects of intraocular pressure reduction in Dutch-belted rabbits treated with 0.02% latrunculin B in citrate-buffered solution (pH ~5.5) containing 4.5% w/v mannitol, 1% w/v polysorbate 80, 0.05% w/v disodium edetate, and 0.01% w/v benzalkonium chloride and with vehicle (Example 4).

Figure 4:
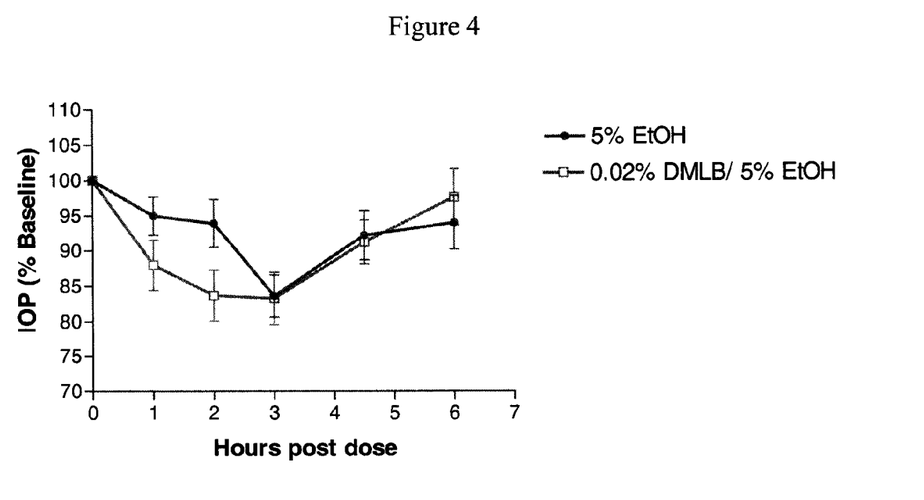
FIG. 4 shows intraocular pressure (IOP, % base line) vs. time post treatment, of Dutch-belted rabbits treated with 0.02% des-methyl latrunculin B in 5% ethanol formulation, and with vehicle.

FIG. 4 shows the effects of intraocular pressure reduction in Dutch-belted rabbits treated with 0.02% des-methyl latrunculin B in 5% ethanol formulation and with vehicle. (Example 5).

Figure 5:
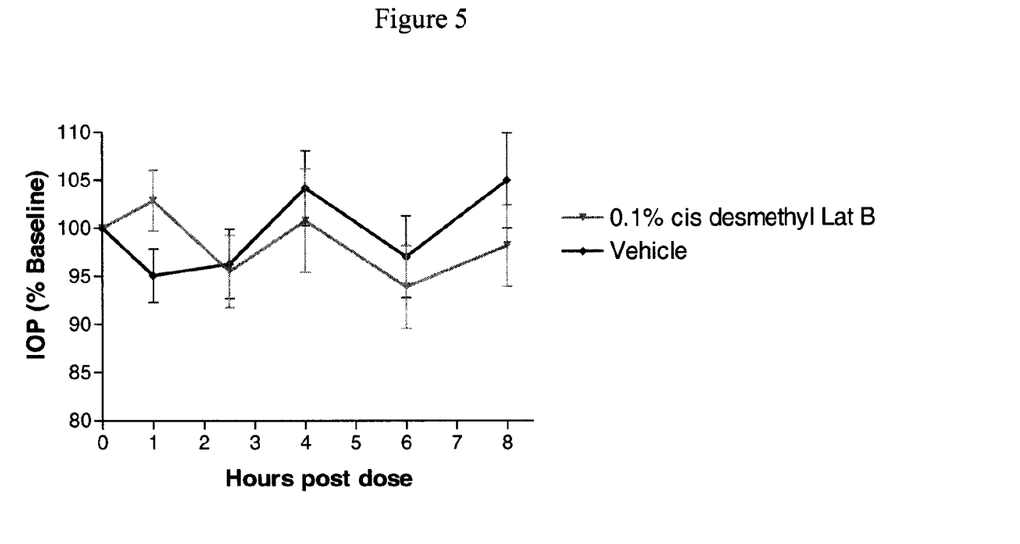
FIG. 5 shows intraocular pressure (IOP, % base line) vs. time post treatment, of Dutch-belted rabbits treated with 0.1% cis-des-methyl latrunculin B in citrate-buffered solution (pH ~5.5) containing 4.5% w/v mannitol, 1% w/v polysorbate 80, 0.05% w/v disodium edetate, and 0.01% w/v benzalkonium chloride, and with vehicle.

FIG. 5 shows the effects of intraocular pressure reduction in Dutch-belted rabbits treated with 0.1% cis-des-methyl latrunculin B in citrate-buffered solution (pH ~5.5) containing 4.5% w/v mannitol, 1% w/v polysorbate 80, 0.05% w/v disodium edetate, and 0.01% w/v benzalkonium chloride and with vehicle. (Example 6).

What is claimed:

1. An aqueous pharmaceutical formulation comprising at least one latrunculin in an amount of 0.001-2% w/v, a non-ionic surfactant in an amount of 0.01-2% w/v, and a tonicity agent to maintain a tonicity between 200-400 mOsm/kG, at a pH between 4 to 8, wherein the latrunculin, the surfactant, and the tonicity agent are compatible in the formulation, the formulation is a clear solution, and the formulation does not contain more than 0.01% of dimethyl sulfoxide and does not contain more than 2% of ethanol.

2. An aqueous pharmaceutical formulation according to claim 1, wherein said formulation does not contain more than 0.001% v/v of dimethyl sulfoxide.

3. An aqueous pharmaceutical formulation according to claim 1, wherein said formulation does not contain any dimethyl sulfoxide.

4. An aqueous pharmaceutical formulation according to claim 1, wherein said non-ionic surfactant is a polysorbate, a polaxamer, or a combination thereof.

5. An aqueous pharmaceutical formulation according to claim 1, further comprising 1-100 mM buffer suitable to maintain the pH between 4-6.

6. The aqueous pharmaceutical formulation according to claim 5, wherein said buffer is citrate buffer, acetate buffer, citrate/phosphate buffer, maleate buffer, tartarate buffer, or combination thereof.

7. The aqueous pharmaceutical formulation according to claim 1, further comprises a chelating agent and/or a preservative.

8. The aqueous pharmaceutical formulation according to claim 1, wherein said tonicity agent is a non-ionic tonicity agent.

9. The aqueous pharmaceutical formulation according to claim 8, wherein said non-ionic tonicity agent is mannitol or dextrose.

10. The aqueous pharmaceutical formulation according to claim 1, wherein said formulation is stable for at least 6 months at 2-8° C.

11. The aqueous pharmaceutical formulation according to claim 1, wherein said latrunculin is latrunculin B.

12. The aqueous pharmaceutical formulation according to claim 1, wherein said latrunculin is latrunculin A, latrunculin B, or des-methyl latrunculin B.

13. The aqueous pharmaceutical formulation according to claim 1, wherein said latrunculin is in an amount of 0.005-0.02% (w/v).

14. The aqueous pharmaceutical formulation according to claim 1, wherein said surfactant is polaxamer in an amount of 0.02-0.25% w/v, and the formulation further comprises 1-10% v/v propylene glycol.

15. An aqueous pharmaceutical formulation comprising at least one latrunculin in an amount of 0.001-2% w/v, a cyclodextrin, a preservative, and a tonicity agent to maintain a tonicity between 200-400 mOsm/kG, wherein the pH of the formulation is 4-8, the formulation is a clear solution, and the formulation does not contain more than 0.01% of dimethyl sulfoxide and does not contain more than 2% of ethanol.

16. A method of reducing intraocular pressure in a mammal, comprising the step of administering to a mammal in need of treatment the aqueous pharmaceutical formulation of claim 1.

17. The aqueous pharmaceutical formulation according to claim 8, wherein said non-ionic tonicity agent is glycerol, polyethylene glycol, or propylene glycol.

18. The aqueous pharmaceutical formulation according to claim 1, wherein said non-ionic surfactant is a polysorbate in an amount of 0.05-1.5% w/v.

19. The aqueous pharmaceutical formulation according to claim 1, wherein said non-ionic surfactant is a polysorbate in an amount of 0.05-1.5% w/v, said non-ionic tonicity agent is mannitol, and said pH is between 4 to 6.

20. The aqueous pharmaceutical formulation according to claim 1, wherein said latrunculin is in an amount of 0.005-0.2% (w/v).

21. The aqueous pharmaceutical formulation according to claim 1, wherein said formulation does not contain more than 1% of ethanol.

22. The aqueous pharmaceutical formulation according to claim 13, wherein said formulation does not contain more than 1% of ethanol.